United States Patent [19]

Grollier et al.

[11] Patent Number: 5,246,693
[45] Date of Patent: Sep. 21, 1993

[54] COSMETIC PREPARATION FOR THE CARE OF THE HAIR AND USE OF THE SAID COMPOSITION

[75] Inventors: Jean-François Grollier; Isabelle Richoux, both of Paris, France

[73] Assignee: L'Oreal, Paris, France

[21] Appl. No.: 627,212

[22] Filed: Dec. 13, 1990

[30] Foreign Application Priority Data

Dec. 13, 1989 [FR] France ................................. 89 16481

[51] Int. Cl.$^5$ ................................................ A61K 7/06
[52] U.S. Cl. ......................................... 424/70; 424/71; 424/401
[58] Field of Search .................... 424/401, 70, 450, 71, 424/63, 195.1; 8/405; 512/2, 3

[56] References Cited

U.S. PATENT DOCUMENTS

| 4,217,344 | 8/1980 | Vanlerberghe et al. | 424/450 |
| 4,358,286 | 11/1982 | Grollier et al. | 8/405 |
| 4,673,567 | 6/1987 | Jizomoto | 424/450 |
| 4,880,621 | 11/1989 | Grollier et al. | 424/63 |
| 4,954,345 | 9/1990 | Müller | 424/450 |
| 5,021,200 | 6/1991 | Vanlerberghe et al. | 424/450 |
| 5,079,227 | 1/1992 | Handjani et al. | 512/3 |

FOREIGN PATENT DOCUMENTS 0347306 12/1989 European Pat. Off. .
2485921 8/1982 France .

OTHER PUBLICATIONS

French Search Report of FR 89 16481.

*Primary Examiner*—Thurman K. Page
*Attorney, Agent, or Firm*—Cushman, Darby & Cushman

[57] ABSTRACT

Cosmetic composition for the care of the hair containing an aqueous dispersion phase, comprising at least one ionic or nonionic amphiphilic lipid associated with at least one stabilising additive and at least one natural or synthetic essential oil. The essential oil represents 0.2 to 20% by weight with respect to the total weight of the composition and the ratio by weight of the lipidic phase to the essential oil(s) is between 0.3 and 10.

16 Claims, No Drawings

COSMETIC PREPARATION FOR THE CARE OF THE HAIR AND USE OF THE SAID COMPOSITION

The present invention relates to a cosmetic composition for the care of the hair and the use of the said composition as a product to be rinsed out or a product which is not to be rinsed out.

It is known that certain amphiphilic lipids are apt to form, in the presence of an aqueous phase, a lamellar phase and then, by agitation, vesicles in dispersion in the said aqueous phase. The vesicles obtained are formed from one or, more often, several concentric layers (bimolecular or multimolecular layers) of lipids encapsulating an aqueous phase. The amphiphilic lipids used can be ionic or nonionic. Such dispersions of vesicles, as well as certain methods of preparing them are described for example in French Patent No. 2 315 991. It has been proposed to use these aqueous dispersions of vesicles of amphiphilic lipids for the treatment of the hair, but these compositions do not make it possible to give the hair a satisfactory smoothness.

It is also known from French Patents Nos. 2 485 921 and 2 490 504 that the vesicles of amphiphilic lipids stabilize in the aqueous phase dispersions of lipids which are not miscible in water, particularly vegetable oils, without it being necessary to add an emulsifying agent. However, the cosmetic compositions obtained with the vegetable oils for the care of the hair have a tendency to soften the hair and make it heavy and it is impossible consequently to obtain a hairstyle which has hold and volume.

The present invention relates to a composition which makes it possible to remedy the aforementioned drawbacks.

The present invention has as its object a cosmetic preparation for the care of the hair, characterized in that it contains in an aqueous phase in continuous dispersion possibly including at least one cosmetically acceptable additive:
a) vesicles prepared from a lipidic phase including at least one amphiphilic lipid which is ionic or non-ionic and is possibly associated with at least one stabilizing additive, the said vesicles containing an encapsulated aqueous phase; and
b) at least one natural or synthetic essential oil in the form of droplets dispersed in the aqueous dispersion phase, the said essential oil(s) being present in a ratio of 0.2 to 20% by weight with respect to the total weight of the composition and the ratio by weight of the lipidic phase to the essential oil(s) being between 0.3 and 10 and preferably between 0.3 and 5.

According to the present invention, it has been found that the compositions according to the invention containing vesicles of amphiphilic lipids and at least one essential oil make the hair smoother and shinier than the compositions which do not contain vesicles of amphiphilic lipids and that the application of these compositions on clean hair, damp or dry, gives a treated effect to the hair without detracting from the lightness nor the shine of a natural hairstyle, which is not the case with the previously described compositions incorporating a combination of vesicles and a vegetable oil which weigh down the hairs and make the style heavy.

The amphiphilic lipids which are capable of forming vesicles are ionic or nonionic lipids. Among the ionic lipids which can be used may be mentioned the natural phospholipids such as lecithin from egg, soya lecithin or sphingomyelin, and the synthetic phospholipids such as dipalmitoyl-phosphatidylcholine or hydrogenated lecithin.

The amphiphilic lipid is preferably a non-ionic lipid and is more preferably constituted by a linear or branched derivative of polyglycerol of formula (I):

$$RO+C_3H_5(OH)O+_{\overline{n}}H \quad (I)$$

in which $-C_3H_5(OH)O-$ represents the following structures in a mixture or separately:

$$-CH_2-CHO-$$
$$\quad \quad |$$
$$\quad \quad CH_2OH$$

and $$-CH-CH_2O-$$
$$|$$
$$CH_2OH$$

$\overline{n}$ is a mean statistical value between 2 and 6 and R is:
a) either an aliphatic chain $R_1$ or an $R_2CO$ radical, $R_1$ being a linear or branched $C_{12}$-$C_{18}$ aliphatic radical and $R_2$ being a linear or branched $C_{11}$-$C_{17}$ aliphatic radical;
b) or $R_3+O-C_2H_3(R_4)+$ where $O-C_2H_3(R_4)-$ represents the following structures in a mixture or separately:

$$O-CH-CH_2$$
$$\quad \quad |$$
$$\quad \quad R_4$$

and $$O-CH_2-CH$$
$$\quad \quad \quad |$$
$$\quad \quad \quad R_4$$

$R_3$ being an $R_1$ or $R_2CO$ radical;
$R_4$ being an $R_1$ radical; and
$R_1$ and $R_2$ having the meanings given above.

According to the invention a mixture of ionic and non-ionic lipids could be used.

It is also possible, apart from the ionic and/or non-ionic amphiphilic lipids described above, to add mixtures consisting in particular of sphingomyelins, cerebrosides, sterols, phosphatidylcholine, phosphatidylserine, phosphatidylethanolamine and glycolipids.

The stabilizing additive is intended in a known manner to modify the permeability and/or the surface charge of the vesicles. It is preferably chosen from amongst the group formed by sterols and anionic stabilisers. The sterol is advantageously cholesterol. The anionic stabilizer is advantageously chosen on the one hand from amongst the monosodium or disodium salts of acylglutamates, the acyl radical having from 14 to 22 C atoms, such as the monosodium salt of stearoylglutamate and the disodium salts with acyl radicals of copra and of tallow or stearoyl and cocoyl radicals, and on the other hand from amongst the phosphoric esters of fatty alcohols having 12 to 22 C atoms. In a known manner it is possible to add sterol and an anionic stabilizer at the same time to the amphiphilic lipid(s).

The vesicles advantageously have a mean dimension between 10 and 1000 nm.

The lipidic phase preferably represents 0.1 to 8% and more preferably 0.25 to 3% of the total weight of the composition; the ionic and/or nonionic amphiphilic lipid(s) preferably represent(s) 0.1 to 6% and more preferably 0.1 to 2.5% of the total weight of the composition; and the stabilizing additive advantageously represents less than 8% of the total weight of the composition and preferably 0.1 to 8% of this weight.

The natural essential oils are products obtained from starting materials of vegetable origin (leaves, stems, flowers, branches of plants and/or entire plants) either by distillation in water vapor, dry or moist, or by mechanical processes, either by distillation to dryness, or by extraction by means of a volatile solvent (see the standard NP-T-75006). The essential oils are distinguished from vegetable oils by the fact that they cannot be decomposed by saponification in glycerol and fatty acid soap.

According to the present invention, the essential oil can be advantageously chosen from amongst the oils of eucalyptus, lavandin, lavender, vetiver, litsea cubeba, lemon, sandalwood, red or white thyme, rosemary, camomile, savory, nutmeg, cinnamon, hyssop, caraway and orange, clove, mint, rose and parsley seeds.

The droplets of essential oil(s) advantageously have a mean dimension between 100 and 10000 nm.

The principal function of the essential oils is to improve the smoothness, the appearance and the style of the hair. However, certain essential oils also have an anti-dandruff effect, action to prevent dropping of the hairs and/or anti-parasite action, particularly against lice; other oils, taken in isolation or in a mixture, have a relaxing or stimulating action.

According to the present application, the encapsulated aqueous phase and/or the lipidic phase of the vesicles can contain substances which are cosmetically and/or pharmaceutically active and which can in particular have the effect of further increasing the known activity of the essential oil. These agents are, for example, agents to prevent dropping of the hair, amongst which may be cited methyl nicotinate, or anti-dandruff agents such as the salt of 1-hydroxy-4-methyl-(2,4,4-trimethyl)-6-pentyl-1H-2-pyridinone ethanolamine.

The dispersion phase of the composition according to the invention can contain at least one thickening agent to facilitate the application and the localization of the compositions on the hair. Amongst the thickening agents which can be used may be cited cellulose derivatives, xanthan gum, and more particularly reticulated polyacrylic acids such as those sold under the brand name "CARBOPOL" (for example "CARBOPOL 934" and "CARBOPOL 940") by GOODRICH.

According to the invention the aqueous dispersion phase can also contain well known cosmetically acceptable additives such as preservatives, perfumes, acidifying agents, alkalinizing agents, stabilizers, colorants and sun filters.

The compositions according to the invention can be used in the form of products to be rinsed out to be applied after shampooing, after coloring or bleaching, after a perm or straightening; in this case the content of essential oil(s) in the composition is preferably between 3 and 20% by weight with respect to the total weight of the composition. The compositions according to the invention can also be used in the form of products which are not to be rinsed out, for example before a set, brushing or finishing the styling; in this case the content of essential oil(s) is preferably between 0.2 and 3% by weight with respect to the total weight of the composition.

The compositions according to the invention are presented in the form of more or less thickened liquids, gels, creams or aerosols.

The examples given below, which are purely by way of illustration and are not limiting, will permit better understanding of the invention.

EXAMPLE 1

Comparative

I) Preparation of the Compositions Tested

A) Preparation of a composition A according to the invention

In a first stage, a mixture of 0.375 g of nonionic lipids of formula:

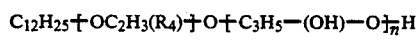

is melted whilst stirring gently at a temperature of 80°-90° C., and in this formula:

—$C_3H_5(OH)O$— is constituted by a mixture of radicals:

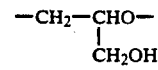

and

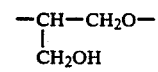

—O—$C_2H_3(R_4)$— is constituted by a mixture of radicals:

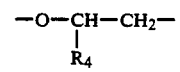

and

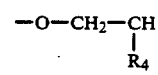

$\bar{n}=6$;

$R_4$ is a mixture of $C_{14}H_{29}$ and $C_{16}H_{33}$ radicals with 0.1 g of Sphingoceryl, which is a mixture sold under this name by "les Laboratoires Sériobiologiques de Nancy", which contains sphingomyelins, cerebrosides, sterols, phosphatidylcholine, phosphatidylserine, phosphatidylethanolamine and glycolipids.

0.95 g of water brought to 90° C., containing a preservative, is introduced into the melted mixture and this is mixed for about 6 to 8 minutes by means of an "ULTRA TURRAX" agitator. 1.43 g of water at ambient temperature is added to the phase thus obtained, then the mixture is homogenized in the "ULTRA TURRAX" for about another 8 minutes before leaving the mixture to return to ambient temperature. A dispersion of vesicles in an aqueous phase is obtained in this way.

In a second stage, 0.375 g of essential eucalyptus oil is added drop by drop to the aqueous phase whilst agitating in the "ULTRA TURRAX". Then a well homogenized aqueous gel consisting of 0.25 g of thickening agent sold under the brand name "CARBOPOL 934" by GOODRICH, dissolved in 5 g of water containing preservatives is added and adjusted to pH 7 with 2-amino-2-methyl-1-propanol and brought to 100 g with water.

B) Preparation of a composition B which does not conform to the invention

A preparation B was prepared which is identical to that described under A but without the addition of essential oil in the second stage.

C) Preparation of a composition C which does not conform to the invention

A preparation C was also prepared which is identical to that described under A except that the essential eucalyptus oil is replaced by colza oil.

II) Comparative Tests

Tests were first of all carried out on a lock of 5 g by applying 0.5 g of composition A to damp and partially dried locks and 0.5 g of composition B to damp locks and then drying for 15 minutes at 60° C. A tactile evaluation was then carried out with a panel of nine testers. Nine testers out of nine found the locks treated with composition A softer.

Comparative tests were also carried out applying compositions A and C. The tests were carried out on the head by applying 2 g of composition A to the dry hair on one half of the head and 2 g of composition B to the dry hair of the other half of the head of a model.

The nine testers declared unanimously that for the 10 models tested they preferred the hair treated with composition A for lightness, shine and for the natural appearance of the hairstyle.

EXAMPLE 2

In a first stage, a mixture of 0.705 g of nonionic lipids of formula:

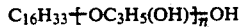

is melted whilst stirring at a temperature of 80°-90° C., in which formula $-OC_3H_5(OH)$ is constituted by a mixture of radicals

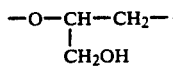

and

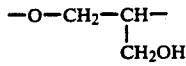

and $\bar{n}$ is a mean statistical value equal to 3, with 0.705 g of cholesterol and 0.09 g of the monosodium glutamate salt of formula:

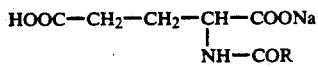

in which R is a mixture of $C_{13}$-$C_{21}$ alkenyl and/or alkyl radicals derived from the fatty acids of tallow, sold under the brand name "ACYLGLUTAMATE HS 11" by AJINOMOTO.

3 g of water brought to 90° C., containing a preservative, is introduced into the melted mixture, and mixing is carried out for about 6 to 8 minutes by means of an "ULTRA TURRAX" agitator. 4.5 g of water at ambient temperature is added to the phase thus obtained, then the mixture is homogenized in the "ULTRA TURRAX" for a further 8 minutes before being left to return to ambient temperature. In this way a dispersion of vesicles in an aqueous phase is obtained.

In a second stage, 1.5 g of a mixture of essential oils (lemon: more than 20%; lavender and sandalwood: from 5 to 20%; white thyme: up to 1%) (proportions by weight) sold under the brand name "COCKTAIL B (HGB 18)" by CHARABOT is added drop by drop whilst agitating in the "ULTRA TURRAX". Then a well homogenized aqueous gel consisting of 0.5 g of a thickening agent sold under the brand name "CARBOPOL 934" by GOODRICH, dissolved in 10 g of water containing preservatives and colorants, is added; the pH is adjusted to 7 with 2-amino-2-methyl-1-propanol and the mixture is made up to 100 g with water.

This composition is applied in a quantity of about 4 to 5 g to the head on hair which has been washed and partly dried. This care composition has an anti-dandruff action and makes it possible to obtain hair which is soft to the touch, light and shiny, with a natural style.

EXAMPLE 3

In a first stage, a mixture of 1.06 g of nonionic amphiphilic lipids of formula:

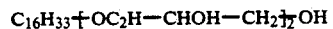

is melted whilst stirring at a temperature of 80°-90° C., with 1.06 g of cholesterol and 0.14 g of the monosodium glutamate salt of formula:

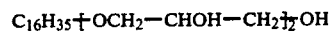

in which R is a mixture of $C_{13}$-$C_{21}$ alkenyl and/or alkyl radicals derived from the fatty acids of tallow, sold under the brand name "ACYLGLUTAMATE HS 11" by AJINOMOTO, and 0.6 g of sphingoceryl.

5.72 g of water brought to 90° C., containing a preservative, is introduced into the melted mixture, and mixing is carried out for about 6 to 8 minutes by means of an "ULTRA TURRAX" agitator. 8.58 g of water at ambient temperature is added to the phase thus obtained, then the mixture is homogenized in the "ULTRA TURRAX" for a further 8 minutes before being left to return to ambient temperature. In this way a dispersion of vesicles in an aqueous phase is obtained.

In a second stage, 2.25 g of a mixture of essential oils (lemon: more than 20%; lavender: more than 20%; hyssop: 1 to 5%; thyme: from 1 to 5%; nutmeg: 1 to 5%) (proportions by weight), this mixture being sold under the brand name "COCKTAIL A (OR 12504)" by MANE, is added drop by drop whilst agitating in the "ULTRA TURRAX". Then a well homogenized aqueous gel consisting of 0.5 g of a thickening agent sold under the brand name "CARBOPOL 934" by GOODRICH, dissolved in 10 g of water containing preservatives and colorants, is added; the pH is adjusted to 7 with 2-amino-2-methyl-1-propanol and the mixture is made up to 100 g with water.

This composition which has, incidentally, an effect of preventing dropping of hair, provides the same cosmetic effects as the composition of example 2.

EXAMPLE 4

In a first stage, a mixture of 0.025 g of nonionic amphiphilic lipids of formula:

$$C_{15}H_{31}\text{+}OCH_2\text{—}CHOH\text{—}CH_2\text{+}_2OH$$

is melted whilst stirring gently at a temperature of 80°–90° C. with 0.225 g of cholesterol and 0.025 g of the monosodium glutamate salt of formula:
in which R is a mixture of $C_{13}$–$C_{21}$ alkenyl and/or alkyl radicals derived from the fatty acids of tallow, sold under the brand name "ACYLGLUTAMATE HS 11" by AJINOMOTO.

0.95 g of water brought to 90° C., containing a preservative, is introduced into the melted mixture, and mixing is carried out for about 6 to 8 minutes by means of an "ULTRA TURRAX" agitator. 1.43 g of water at ambient temperature are added to the phase thus obtained, then the mixture is homogenized in the "ULTRA TURRAX" for a further 8 minutes before being left to return to ambient temperature. In this way a dispersion of vesicles in an aqueous phase is obtained.

In a second stage, 0.375 g of essential eucalyptus oil is added drop by drop whilst agitating in the "ULTRA TURRAX". Then a well homogenized aqueous gel consisting of 0.25 g of a thickening agent sold under the brand name "CARBOPOL 934" by GOODRICH, dissolved in 5 g of water containing preservatives and colorants, is added; the pH is adjusted to 7 with 2-amino-2-methyl-1-propanol and the mixture is made up to 100 g with water.

This care composition provides the same cosmetic effects as the composition of example 2, that is to say the hair is soft to the touch, light and shiny, with a natural appearance.

EXAMPLE 5

In a first stage 0.5 g of soya lecithin is melted whilst stirring gently at a temperature of 60° C. to 75% of phosphatidylcholine sold by SEPPIC under the brand name "LIPOID S75".

0.96 g of water brought to 80° C., containing a preservative, is introduced into the melted mixture, and mixing is carried out for about 5 minutes by means of an "ULTRA TURRAX" agitator, then the mixture is left to swell for one hour. 1.44 g of water at 20° C. are added to the phase thus obtained; the the mixture is agitated for several minutes with the aid of the same agitator. It is completed by 0.7 g of water at 20° C. whilst agitating in the "ULTRA TURRAX".

In this way a dispersion of vesicles in an aqueous phase is obtained.

In a second stage, 0.4 g of a mixture of essential oils sold by MANE under the brand name "COCKTAIL C (OR 12509)" is added drop by drop whilst agitating in the "ULTRA TURRAX"; this mixture of essential oils is defined as follows (by weight):

| lemon | more than 20% |
|---|---|
| clove | 1 to 5% |
| mint | 1 to 5% |
| rose | 1 to 5% |
| lavender | 5 to 20% |

Then a well homogenized aqueous gel consisting of 0.5 g of a thickening agent sold under the brand name "CARBOPOL 934" by GOODRICH, dissolved in 10 g of alcohol at 96° containing preservatives and colorants, is added; the pH is adjusted to 7 with 2-amino-2-methyl-1-propanol and the mixture is made up to 100 g with water.

This composition is applied in a quantity of about 4 to 5 g to the head on hair which has been washed and partly dried. This composition, which incidentally has a relaxing action, provides the same cosmetic effects as the composition of example 2.

EXAMPLE 6

In a first stage, 0.4 g of polyoxyethylene phytosterol is melted whilst stirring gently at 85° C. with 5 mole ethylene oxide 4 sold by HENKEL under the brand name "GENEROL 122E 5", then to the melted mixture is added 0.6 g of hydrogenated lecithin to 30–35% hydrogenated phosphatidyloholine sold by NIKKO under the brand name "LECINOL S 10" until perfect homogenization is achieved (5 minutes).

3 g of water brought to 80° C., containing a preservative, is introduced into the melted mixture, and mixing is carried out for about 5 minutes by means of an "ULTRA TURRAX" agitator, then the mixture is left to swell for one hour. 4.5 g of water at 20° C. are added to the phase thus obtained; the the mixture is again agitated for several minutes with the aid of the same agitator. In this way a dispersion of vehicles in an aqueous phase is obtained.

In a second stage, 0.5 g of a mixture of essential oils sold by ROBERTET under the brand name "COCKTAIL F (8388)" is added drop by drop whilst agitating in the "ULTRA TURRAX"; this mixture of essential oils is defined as follows (by weight):

| lavender | more than 75% |
|---|---|
| Morocco camomile | 1 to 5% |
| Florida orange | 1 to 5% |
| parsley seeds | 1 to 5% |
| rose | 5 to 20% |

Then a well homogenized aqueous gel consisting of 0.5 g of a thickening agent sold under the brand name "CARBOPOL 934" by GOODRICH, dissolved in 10 g of alcohol at 96° containing preservatives and colorants, is added; the pH is adjusted to 7 with 2-amino-2-methyl-1-propanol and the mixture is made up to 100 g with water.

This composition is applied in a quantity of about 4 to 5 g to the head on hair which has been washed and partly dried. This composition, which incidentally has a relaxing action, provides the same cosmetic effects as the composition of example 2.

We claim:
1. A method for treating hair comprising the steps of:
i) applying to said hair a composition comprising, in a continuous aqueous phase, a dispersion of
a) vesicles prepared from a lipidic phase comprising at least one amphiphilic ionic or nonionic lipid material encapsulating an aqueous phase, and b) at least one natural or synthetic essential oil in the form of droplets, said essential oil being present in an amount ranging from 0.2 to 20 percent by weight based on the total weight of said composition, and the weight ratio of said lipidic phase to said essential oil is between 0.3 to 10; and ii) rinsing said hair.

2. The method of claim 1 wherein said lipidic phase of (a) is associated with at least one stabilizing additive selective from a sterol and an anionic stabilizer.

3. The method of claim 1 wherein the weight ratio of said lipidic phase to said essential oil is between 0.3 and 5.

4. The method of claim 1 wherein said amphiphilic lipid is a nonionic lipid material constituted by a linear or branched derivative of polyglycerol having the formula $$RO-[C_3H_5(OH)O]_{\overline{n}}H \qquad (I)$$

wherein $-C_3H_5(OH)O-$ represents the following structures, in a mixture or separately:

$$-CH_2-CHOH-CH_2O-,$$

$$-CH_2-CHO- \text{ and}$$
$$\qquad |$$
$$\qquad CH_2OH$$

$$-CH-CH_2O-,$$
$$\;|$$
$$CH_2OH$$

$\overline{n}$ has a mean statistical value ranging from 2 to 6, and R represents (a) an aliphatic chain $R_1$ or an $R_2CO$ radical wherein $R_1$ represents a linear or branched $C_{12}-C_{18}$ aliphatic radical and $R_2$ represents a linear or branched $C_{11}-C_{17}$ aliphatic radical, or (b) $R_3-[-O-C_2H_3(R_4)-]-$ wherein $O-C_2H_3(R_4)-$ represents the following structures, in a mixture or separately:

$$O-CH-CH_2$$
$$\quad |$$
$$\quad R_4$$

and $$O-CH_2-CH$$
$$\qquad\quad |$$
$$\qquad\quad R_4$$

wherein
$R_3$ represents a $R_1$ or $R_2CO$ radical and
$R_4$ represents a $R_1$ radical,
$R_1$ and $R_2$ having the meanings given above.

5. The method of claim 1 wherein said lipidic phase comprises a mixture of amphiphilic ionic and nonionic lipid materials.

6. The method of claim 2 wherein said sterol is cholesterol.

7. The method of claim 2 wherein said anionic stabilizer is selected from a monosodium acyl glutamate salt, wherein the acyl moiety has 14–22 carbon atoms, a disodium acyl glutamate salt, wherein the acyl moiety has 14–22 carbon atoms, and a phosphoric ester of a fatty alcohol having 12–22 carbon atoms.

8. The method of claim 1 wherein said lipidic phase represents from 0.1 to 8 percent by weight based on the total weight of said composition.

9. The method of claim 1 wherein said amphiphilic lipid material represents from 0.1 to 6 percent by weight based on the total weight of said composition.

10. The method of claim 2 wherein said stabilizing additive represents less than 8 percent by weight based on the total weight of said composition.

11. The method of claim 1 wherein said essential oil is selected from the group consisting of eucalyptus oil, lavandin oil, vetiver oil, litsea cubeba oil, lemon oil, sandalwood oil, red thyme oil, white thyme oil, camomile oil, savory oil, nutmeg oil, cinnamon oil, hyssop oil, caraway oil, orange oil, clove oil, mint oil, rose oil and parsley seed oil.

12. The method of claim 1 wherein said encapsulated aqueous phase or said lipidic phase, or both, contains a cosmetically or pharmaceutically active substance.

13. The method of claim 1 wherein said continuous aqueous phase also contains at least one additive selected from the group consisting of a thickening agent, a preservative, an acidifying agent, an alkalinizing agent, a stabilizer, a colorant, and a sun filter.

14. The method of claim 1 wherein said vesicles have a mean dimension ranging from 10 to 1,000 nm and said droplets of said essential oil have a mean dimension ranging from 100 to 10,000 nm.

15. The method of claim 1 wherein said essential oil is present in an amount ranging from 3 to 20 percent by weight based on the total weight of said composition.

16. The method of claim 1 wherein said essential oil is present in an amount ranging from 0.2 to 3 percent by weight based on the total weight of said composition.

* * * * *